United States Patent [19]

Hutton et al.

[11] Patent Number: 4,567,010

[45] Date of Patent: Jan. 28, 1986

[54] GRANULATION

[75] Inventors: Denis A. Hutton, Sale; Malcolm H. Millar, Widnes, both of England

[73] Assignee: Interox Chemicals Limited, London, England

[21] Appl. No.: 410,988

[22] Filed: Aug. 24, 1982

[30] Foreign Application Priority Data

Sep. 8, 1981 [GB] United Kingdom ............. 8127157

[51] Int. Cl.$^4$ ............................................. C09C 1/56
[52] U.S. Cl. .................................. 264/117; 252/95; 252/174.24
[58] Field of Search ................ 252/95, 174.24; 568/558, 559, 566; 562/493; 23/313 FB, 313 P; 264/117

[56] References Cited

U.S. PATENT DOCUMENTS

| | | | |
|---|---|---|---|
| 3,494,787 | 2/1970 | Lund et al. | 252/89 |
| 4,134,725 | 1/1979 | Buchel et al. | 252/174 |
| 4,372,868 | 2/1983 | Saran et al. | 264/117 |
| 4,385,008 | 5/1983 | Hignett | 562/492 |
| 4,403,994 | 9/1983 | Hignett | 252/95 |
| 4,414,130 | 11/1983 | Cheng | 264/117 |

FOREIGN PATENT DOCUMENTS

| | | |
|---|---|---|
| 27693 | 4/1981 | European Pat. Off. |
| 66992 | 12/1982 | European Pat. Off. |
| 893115 | 5/1944 | France. |

OTHER PUBLICATIONS

Abstract of JA 50/91596, 1975.

*Primary Examiner*—Hiram H. Bernstein
*Attorney, Agent, or Firm*—Larson and Taylor

[57] ABSTRACT

Granules of the magnesium salts of percarboxylic acid carboxylates are obtained by spraying onto agitated feed particles of the salt a small amount of a dilute aqueous solution of a synthetic poly hydroxy-substituted compound, particularly polyvinylalcohol and drying the resultant agglomerate. It is especially suitable to carry out the granulation process in a warm air fluidized bed using feed particles of mainly below 200 microns producing eventually a low bulk density product mainly in the range 200–1000 microns.

In a modification of the fluidized bed process, the agglomerating agent used can be a aqueous solution of carboxylated polyvinyl alcohol.

17 Claims, No Drawings

GRANULATION

The present invention relates to a process for the granulation of peroxygen compounds and the granules obtained thereby, and in particular to such a process and granules in which the peroxygen compounds is a magnesium salt of an organic peroxyacid carboxylate.

In European Patent Specification No. 27693 in the name of Interox Chemicals Limited there are described and claimed certain magnesium salts which are useful inter alia as bleaching agents and are:

In solid form, the magnesium salt of:

Class (1)—an aromatic carbocyclic compound substituted around the aromatic nucleus of a carboxylate group and a peroxycarboxylic acid group both groups being derivable from the corresponding aromatic carbocyclic anhydride by reaction with hydrogen peroxide, said aromatic carboxylic compound optionally being further substituted by at least one of the groups selected from alkyl, carboxylate, sulphonate, nitro, chloro and bromo groups or Class (2)—a cycloaliphatic compound substituted around the cycloaliphatic nucleus by a carboxylate group and a peroxycarboxylic acid group both groups being derivable from the corresponding cycloaliphatic carbocyclic anhydride by reaction with hydrogen peroxide, said cycloaliphatic carboxylic compound optionally being further substituted by at least one of the groups selected from alkyl, carboxylate, sulphonate, nitro, chloro and bromo groups or Class (3)—an olefinically unsaturated aliphatic compound substituted by a carboxylate group and a peroxycarboxylic acid group, the carbonyl group of the carboxylate substituent being conjugated with the carbonyl group of the peroxycarboxylic acid via the olefinic unsaturation within the aliphaticc compound, both substituents being derivable from the corresponding anhydride by reaction with the hydrogen peroxide.

The specification also describes the manufacture of such salts by reaction between an anhydride, aqueous hydrogen peroxide and a magnesium base in an inert organic reaction medium such as ethyl acetate. In many instances, the solid product obtained directly in such a process has a lower average particle size than would be preferred for incorporation in detergent powder compositions.

In unpublished European Patent Application No. 82302605.9 also in the name of Interox Chemicals Limited there is described an alternative method for manufacturing magnesium salts of classes (1) and (3) defined hereinabove in which the solid salt is precipitated from a substantially aqueous medium. In many instances the product is obtained with a higher average particle size than from the inert organic reaction medium. Whilst this is advantageous from the viewpoint of its incorporation and non-segregation in detergent compositions, the measured rate of solubility of the salt was found to decline as the average size increased.

Investigations were made into ways of granulating or agglomerating small particles of the magnesium salts to produce granules within which term is included agglomerates. In view of the superior solubility of the magnesium salts in comparison with conventional solid peroxygen bleaches, e.g. sodium perborate tetrahydrate and sodium percarbonate at temperatures at or near ambient, it might be expected that agglomeration could readily be carried out using water alone, but agglomeration of the magnesium salts does not occur when using a fluidised bed granulator and when using a pan ball granulator the resultant product has an impaired solubility.

It will be recognised that many inorganic and organic compounds have been suggested in the past as granulating aids or coating agents for solid peroxygen compounds. There have been included amongst the classes of inorganic compounds, a solution of the peroxygen compound itself or its non-peroxygenated analogue and amongst the classes of organic compounds glycol polymers. When compounds within such classes, such as magnesium phthalate and polyethyleneglycol were tried as granulating aids in granulation of the magnesium salts herein using a fluidised bed the resultant product in general was little different from when water alone was used, i.e. little or no granulation occurred. This was demonstrated by no more than a small amount of product of acceptable particle size being obtained, and even that product being unacceptably friable. A similarly poor result was obtained when dextrin or isinglass or a gum such as gum acacia described as coating agents in French Patent Specification 893115, were used.

In addition, when a commonly used coating agent for inorganic persalts was used, namely sodium silicate solution, e.g. as described in Japanese Patent Publication No. 78/15716 in conjunction with dextrin, substantial decomposition of the magnesium persalts occurred. Other agents such as sodium or magnesium sulphate, described as coating agents for perphthalic acids in U.S. Pat. No. 3494787 et aliter have virtually no or little positive effect on the friability of the product. This demonstrates that it is not possible to transfer granulating technology directly from one group of peroxygen compounds to the magnesium salts described herein with any reasonable predictability. Consequently all the many published patent specifications from said French Patent Specification No. 893115 to H. Guiot onwards are of background guidance to what has been tried for other percompounds and cannot act as a clean pointer to what should be used for the instant magnesium persalts.

According to the present invention there is provided a process for granulating particles of one or more of the magnesium salts of organic peroxyacid carboxylates described hereinbefore, comprising the steps of agitating the particles, thereby bringing them into contact with each other from time to time whilst simultaneously spraying onto the agitated particles an aqueous solution of an hydroxylated organic polymer to provide at least 0.1% of polymer based on the dry product, and drying the product, maintaining the temperature of the particles throughout the process at not more than 65° C.

Herein, the invention will be described with particular reference to the magnesium salt of monoperoxyphthalic acid which is an hydrated salt having empirical formula:

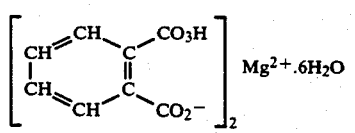

The other magnesium salts of classes (1), (2) and (3) can likewise be employed in the invention, mutatis mutandis.

It is highly desirable to employ as the hydroxylated organic polymer, a synthetic polymer obtained from an hydroxyl-substituted monomer or monomer in which the hydroxyl group is masked and is subsequently unmasked after polymerisation, of which one very acceptable class comprises polyvinylalcohols (PVA). The PVA polymer desirably has an average degree of polymerisation of at least 500, preferably at least 1,000 and in many preferred embodiments at least 1,500. Generally the PVA polymer has an average degree of polymerisation of not more than 4,000 and often less than 3,000. In particularly preferred embodiments the average degree of polymerisation of the PVA polymer is from 1,500 to 2,500. It will be recognised that a blend of two or more PVA polymers can be employed, for example one containing a minor proportion of a lower molecular weight polymer such as 5 to 15% w/w of a polymer having a degree of polymerisation of 500 to 1,000 and the balance of the polymer blend having a degree of polymerisation of 1,500 to 2,500, possibly containing also if desired a small proportion of PVA having an even higher degree of polymerisation. As an alternative to using a preformed blend, two or more polymer solutions can be added separately either simultaneously or sequentially, with preferably the lower molecular weight polymer being added first. The PVA polymer used is typically one that has been hydrolysed to above 80%, and those hydrolysed to 87–90% have been employed most successfully. It has been found that the carboxylated derivatives of the PVA polymers can be used successfully also.

The polymer is usually employed in aqueous solution at a concentration so selected that the solution can be sprayed using the selected apparatus. Naturally, the maximum concentration usable is dependent upon the molecular weight of the polymer and the temperature of the solution. Typically, the concentration of polymer is selected in the range of 1 to 12% by weight. For a polymer having a degree of polymerisation in the region of 2,000, a very effective concentration of polymer is thus in the region of 4 to 5% by weight. Conveniently, the solution can be employed at ambient temperature, but if desired the solution can be sprayed in at a temperature of up to 65° C.

The amount of agglomerating agent employed is normally selected within the range of 0.1 to 5% of polymer often at least 0.2% and in many cases at least 0.5% percentages of polymer used herein being by weight, based on the dried products. In practice, it is preferable to employ up to about 2.5%, of polymer, the amount often being selected in the range of 0.8 to 2.0% of polymer. It will be understood that as a general rule, the more agglomerating agent that is added, the larger is the average particle size of the resultant dried product, but that to some extent, there is a tendency for existing agglomerates to grow rather than for new agglomerates to be formed. Naturally, the amount of agglomerating agent is selected taking into account the average size of the feed particle and the desired size of the product. We have found that it is suitable to select the amount within the range of 0.3% to 2.0% and particularly 0.8% to 1.5% by weight of the dried product, where it desired to produce an agglomerate of which a substantial proportion has a particle size in the range of 0.15 to 1.0 mm employing a feed containing at least 75% by weight of particles of less than 0.2 mm diameter, the feed preferably containing at least 80% by weight of particles of less than 0.15 mm diameter.

After the agglomerate has been dried, it is often preferable to sieve it so as to isolate a fraction having a specified range of particle sizes, for example the aforementioned range or a narrower one of 0.2 mm to 0.85 mm. Underside particles (fines) can be recycled to the agglomerator. Oversize particles can be crushed or milled, preferably only to the extent of obtaining a substantial proportion of agglomerates within that specified range of particle sizes, any fines resulting, again being recycled.

Substantially all the feed material for the agglomeration process of the present invention has a particle size of below 0.5 mm and in practice a large proportion of the particles is usually below 0.2 mm, in many instances from 75 to 90% by weight or even higher. It is most convenient to employ a feed having a weight measured geometric mean particle diameter of 75 to 100 microns. The particles can be obtained from the processes described in the aforementioned patent applications. Where otherwise they would be larger than preferred, they can be crushed or milled. As desired, the feed can be either dry or wet, the actual operating conditions being adjusted to take into account the free water content of the particles. It can be convenient to employ for example, damp solid obtained from the filter or centrifuge in the route described in EPA No. 82302605.9, possibly after gentle crushing or alternatively or additionally to employ dried and where needed milled particles of the magnesium salt. It will be understood that a proportion of the feed particles can be particles of similar size of materials compatible with the aforementioned magnesium salts of classes (1), (2) and (3). Such materials could desirably be selected from the compounds described in said European Patent Specification No. 27693 as being a particularly important class of desensitising diluents and comprising the alkali metal or alkaline earth metal salts of halogen-free acids having a first dissociation constant of at least $1 \times 10^{-3}$ for example sodium or magnesium sulphate or the various sodium phosphates. It will also be understood that the particles of magnesium salt, by virtue of their method of manufacture can often contain some additional substance, such as the magnesium salt of the corresponding nonperoxygenated acid, which in the case of magnesium monoperoxyphthalate is magnesium phthalate, and/or possibly various crystal modifiers.

In one important aspect of the present invention a particular feature is the use of an inert gas for agitating the particles and especially using the gas to fluidise a bed of the particles. By so doing, it is possible to obtain agglomerates of magnesium salt particles that have an apparent free flowing bulk density somewhat lower than when employing, for example rotating pan or drum granulators. This can be of especial benefit where the agglomerates are intended for incorporation in powder detergent compositions in that such a bulk density can more closely match that of spray-dried products which generally form a substantial proportion of such compositions and thereby minimise bleach/detergent segregation within the composition during handling. Consequently, according to one aspect of the invention there is provided an agglomerate of one or more magnesium salts described hereinbefore, and especially magnesium monoperoxyphthalate having a particle size in the range of 0.2 to 1.0 mm, a weight averaged particle size in the range of 0.4 to 0.65 mm and an apparent free flowing bulk density within the range of 0.3 to 0.6 kg/l, particularly when obtained by the agglomeration of feed particles of the magnesium salt of which at least 75% by weight are below 0.2 mm and preferably at least 80% by weight are below 0.2 mm. Such agglomerates can be produced in particular by the use of a fluidised bed granulator in conjunction with the hydroxyl substituted organic polymer especially PVA and carboxylated PVA described herein.

The inert gas employed to agitate te particles is most conveniently air, but it can be nitrogen or any other gas that does not react with the magnesium salt or the agglomerating agent under the conditions of contact. In practice, of course, the influent inert gas is unsaturated with respect to water vapour, an effect which occurs naturally when the gas is heated and/or dried before being used to agitate the particles.

In a fluidised bed process, the bed of magnesium salt particles is fluidised throughout by an updraft of the inert gas, typically air, and the gas flow is adjusted in accordance with the particles' sizes and weights as in conventional practice to maintain the particles in suspension in the fluidising chamber, and where possible not to carry out therefrom more than a very minor proportion of the particles, which can be subsequently separated off often using e.g. blowback filters, such control and operation of a fluidised bed being well known and needing no further clarification herein.

In batch operation, granulation in the fluidised bed comprises the stages of charging a fluidising chamber with a bed of feed particles of magnesium salt, and bringing the bed of particles to a desired temperature, spraying agglomerating agent in aqueous solution into or preferably onto the bed, drying the bed and generally cooling the bed before discharging the granulates. It will be recognised that the various stages can be effected in the same or different chambers and that alternatively, the process can be carried out continuously using a segmented chamber or plurality of chambers in which, for example, the feed particles and/or agglomerates, as the case may be, pass from one segment or chamber to the next by, for example, overflow over a weir.

Preferably, the inert gas is employed at an inlet temperature of from 40° to 80° C. especially at least 50° C., and most preferably from 60° to 65° C. during the stages prior to cooling. During the cooling stage, the gas temperature at the inlet can be lowered progressively or immediately to within the range of below 30° C., typically from 5° to 25° C. and most conveniently ambient.

The bed of particles is preferably brought to a temperature in the range of 35° to 50° C., often from 40° to 45° C. prior to being sprayed. During the spraying stage, the bed is maintained at a temperature of at least 25° C. and usually not above 50° C. by heat supplied by the fluidising gas and optionally by heating elements disposed within or around the fluidising chamber having contact surfaces preferably not above 65° C. As is well known in the art the rate of introduction of the aqueous solution of agglomerating agent into the fluidised bed is controlled in conjunction with the flow of the fluidising gas and other bed parameters so as to maintain the bed in a fluidised condition and thus avoid the condition known as "wetting out". Such control is within the competence of the skilled man, and takes into account external conditions such as the temperature and humidity of the ambient air. In practice we find it convenient on many occasions to introduce the agglomerating agent solution gradually over a limited period of at least 20 minutes and often within the range of 20 to 30 minutes, and to maintain a temperature in the region of about 30° C., typically 28° to 33° C. Alternatively, the solution can be introduced in small increments rather than continuously. The solution is introduced in the form of a spray and as is known, some variation in the particle size of the granulate can be obtained by variation in the size of the spray droplets. We have found it particularly convenient to spray from a jet having orifices of diameter selected within the range 1.2 mm to 2.4 mm and an atomising air pressure selected in the range of 1 to 4 bar, especially at about 1.8 mm at an atomising air pressure of 1.8 bar, or other equivalent orifices/atomising pressures combinations, depending inter alia upon the scale of operation.

The agglomerates are very preferably dried in the fluidised bed so as to avoid the formation of cakes which might otherwise occur if they were discharged wet from the bed. The drying is preferably carried out until the effluent gas has attained a steady temperature, the precise value of which will depend, naturally, upon the influent gas temperature and the apparatus itself. When influent gas at 60°–65° C. is employed, an effluent gas temperature from the filters usually blow-back filter of up to about 55°–60° C. is typical. The drying time is generally within the range of 5 to 20 minutes when carried out in the bed. The subsequent cooling with cool gas often lasts a further 5 to 10 minutes, and thus in total the granulation process normally takes from 40 to 80 minutes, often 45 to 60 minutes from the start of introduction of the agglomerating agent.

By the use of the fluidising bed granulation process, and where desired appropriate sieving afterwards especially to remove residual fines, a granular product can be obtained that meets the criteria for particle size and bulk density described hereinbefore. Advantageously, the product of such a process is free flowing and its resistance to attrition can be judged from the fact that it has survived the abrasive conditions prevalent in a fluidised bed, but further improvement can be obtained by including a grinder within the bed, if desired. Furthermore, the product tends to cause in general, less dye damage when washing than does a product of comparable particle size but higher density obtained using a pan ball granulator. Finally, it has been found that by carrying out the fluidised bed granulation quickly in the manner described herein the resultant product loses no more than a small proportion of its available oxygen (avox), in many cases being less than 5% loss leaving often a product containing at least 6% avox which is similar to that in the feed particles.

The product of the present invention can be readily incorporated in bleaching and detergent compositions.

Having described the invention in general terms, specific embodiments thereof will now be described by way of example and without limitation. Modifications thereof in accordance with the foregoing disclosure or with the background skill and knowledge of the artisan can be made without departing from the spirit of the invention.

In the Examples, the feed particles were obtained by milling through a cross beater mill fitted with a 2 mm screen, a dried sample of magnesium monoperoxy phthalate produced substantially in accordance with a scaled-up version of Example 17 of British Patent Application No. 8117841. On analysis, about 90% of the feed particles by weight had a diameter of below 212 microns after milling.

In each batch, a small pilot scale fluidised bed chamber was charged with approximately 15 kg of the feed particles at ambient temperature and then the bed was fluidised with an updraft of hot air, having an inlet temperature maintaned within the range of 60°-65° C. The bed temperature was monitored, and when it had reached 40° C., introduction commenced of an aqueous solution of polyvinyl alcohol having an average molecular weight of about 2400 to 2500 (ambient temperature of about 20°, 4% concentration by weight) through a jet having nominal apertures of 1.8 mm under a pressure of 1.8 bar. 2000 mls of solution were sprayed in during the next 20 to 30 minutes. The bed temperature fell slightly during the spraying by virtue mainly of evaporation but was maintained at near 30° C. throughout. Fluidisation with the warm air continued for about 15 minutes or so after introduction of polyvinylalcohol solution ceased, by which time the bed temperature had risen to 55° to 57° C. and the air at the outlet had attained a steady temperature of about 40° C., indicating that the bed was substantially dry. The bed was then fluidised for a few minutes with ambient air and when the granules had cooled to 35° to 40° C., the product was discharged and then roughly sieved. Typically, the yield of product in the nominal range of +212 microns to −710 microns was about 7.5 kg, that of −212 microns was about 4.5 kg and that of +710 microns was about 3 kg. The oversize material was milled in the aforementioned mill to yield a further 40% of product in the range +212 to −710 microns and the undersize material was recycled.

The product in the preferred range had a free-flowing apparent bulk density, measured substantially in accordance with the method and apparatus descibed in British Patent Specification No. 1600106, and when it was substantially free from retained undersize particles which was in the range of 0.35 to 0.41 kg/l. The solubility of the product was measured by stirring 0.25 g solid at 50 rpm in 25 ml water at 20° C. in a centrifuge tube for 15 seconds, centrifuging the tube for 30 seconds, and finally decanting off the supernatant liquid and measuring its available oxygen (avox) content. By comparing the dissolved avox with the known avox of the solid product, the solubility of active oxygen can then be calculated. Typically, the invention product in the preferred particle size range had a solubility in the range 70 to 90% by weight, whereas when the same test was carried out on pan ball granulated material, the solubility was only just over 50% by weight, which is considerably worse. That same pan ball granulated product also tended to have a higher apparent bulk density, generally from 0.6 to 0.7 kg/l.

Substantially the same results were obtained when the Example was repeated using the same fluid bed apparatus and conditions except that the magnesium monoperoxyphthalate feed particles had a weight geometric mean of about 90 microns and various other sources of polyvinyl alcohol having average degrees of polymerisation varying from 1700 to 2400, degrees of hydrolysis about 88% were used, as before in aqueous solution, providing a 1% w/w loading of polymer on the dry product. Such products not only had acceptable rates of solubility but also an acceptable resistance to attrition.

In a modification, the Example was repeated using a futher sample of the latter batch of magnesium salt feed particles, and as binding agent an aqueous solution of a carboxylated derivative of PVA. At a loading of 2% on the dry product, there was a tendency of oversize product to form, but it had excellent resistance to attrition and good solubility. This indicates that the carboxylated derivative of PVA is substantially as effective a binder for the present purpose as PVA itself.

By way of comparison, the Example was also repeated using the same apparatus and conditions and latter feed particles, but using other binding agents in aqueous solution. Gum acacia, isinglass, magnesium phthalate, sodium sulphate, methyl cellulose, and dextrin all could granulate only a small fraction of the feed particles, and even those granules were easily attrited.

We claim:

1. A process for granulating particles of one or more magnesium salts of an organic peroxyacid carboxylate, comprising the steps of agitating the particles, thereby bringing them into contact with each other from time to time whilst simultaneously spraying onto the agitated particles an aqueous solution of an hydroxylated organic polymer selected from the group consisting of polyvinylalcohol and carboxylated derivatives thereof to provide at least 0.1% of polymer based on the dry product, and drying the product, maintaining the temperature of the particles throughout the process at not more than 65° C.

2. A process according to claim 1 in which the polymer is synthetic.

3. A process according to claim 1 in which the polyvinyl alcohol has an average degree of polymerisation of from 1000 to 3000, preferably 1500 to 2500.

4. A process according to claim 1 or 3 in which the polymer is employed at a concentration in the aqueous solution selected in the range of from 1 to 12% by weight.

5. A process according to claim 1 or 3 in which the amount of polymer employed is selected in the range of from 0.5 to 2.5%, and preferably 0.8 to 2.0% by weight based upon the dried granular product.

6. A process according to claim 1 in which the polymer is polyvinylalcohol or a blend thereof having an average degree of polymerisation of 1500 to 2500 sprayed into the particles at a concentration in the aqueous solution of 4 to 5% by weight in such an amount that the dried granulated product contains 0.8 to 2.0% by weight of the polymer.

7. A process according to claim 1 in which the particles are agitated and fluidised in a bed by an inert fluidising gas, the bed being maintained at a temperature of at least 25° C. during the introduction of the aqueous solution of polymer.

8. A process according to claim 7 in which the bed is maintained at a temperature of 28°-33° C. during the introduction of the aqueous solution of polymer.

9. A process according to claim 8 in which the fluidising gas has an inlet temperature of from 50° to 60° C.

10. A process according to any of claims 7, 8 or 9 in which the agglomerates formed are subsequently dried in a fluidised bed preferably until the effluent fluidising gas has attained a substantially constant temperature.

11. A process according to claim 10 in which the dried agglomerates are subsequently cooled to below 40° C. by fluidisation with cool fluidising gas before discharge from the bed.

12. A process according to claim 7 in which the particles are sprayed with an aqueous solution of polyvinylalcohol having an average degree of polymerisation of from 1000 to 3000, preferably 1500 to 2500 said solution having a concentration selected in the range of 1 to 12% by weight and in an amount calculated to provide from 0.5 to 2.5% by weight polymer in the dried granular product.

13. A process acording to claim 8 in which the particles are sprayed with an aqueous solution of polyvinylalcohol having an average degree of polymerisation of from 1000 to 3000, preferably 1500 to 2500 said solution having a concentration selected in the range of 1 to 12% by weight and in an amount calculated to provide from 0.5 to 2.5% by weight polymer in the dried granular product.

14. A process according to claim 1, 12 or 13 in which the fraction of the product having a particle size of from 0.15 to 1.0 mm is subsequently isolated.

15. A process according to claim 1 in which at least 75% of feed particles are less than 0.2 mm diameter.

16. A process according to claim 12 or 13 in which the feed particles have a geometric mean diameter of 75 to 100 microns, the agglomerates formed are subsequently dried in a fluidised bed prererably until the effluent fluidising gas has attained a substantially constant temperature and the dried agglomerates are subsequently cooled to below 40° C. by fluidisation with cool fluidising gas before discharge from the bed.

17. A process according to claim 1, 6, 7, 12 or 13 in which the magnesium salt is magnesium monoperoxyphthalate.

* * * * *